(12) United States Patent
Tamaoki et al.

(10) Patent No.: US 7,785,867 B2
(45) Date of Patent: Aug. 31, 2010

(54) CULTURE DEVICE AND STORAGE CONTAINER

(75) Inventors: Yuichi Tamaoki, Gunma (JP); Takashi Arai, Gunma (JP); Tadahisa Saga, Gunma (JP); Hiroki Busujima, Ota (JP)

(73) Assignee: Sanyo Electric Co., Ltd., Moriguchi-Shi (JP)

( * ) Notice: Subject to any disclaimer, the term of this patent is extended or adjusted under 35 U.S.C. 154(b) by 1016 days.

(21) Appl. No.: 10/503,137

(22) PCT Filed: Feb. 19, 2003

(86) PCT No.: PCT/JP03/01745

§ 371 (c)(1),
(2), (4) Date: Aug. 11, 2004

(87) PCT Pub. No.: WO03/070874

PCT Pub. Date: Aug. 28, 2003

(65) Prior Publication Data

US 2005/0084955 A1 Apr. 21, 2005

(30) Foreign Application Priority Data

Feb. 22, 2002 (JP) ............................. 2002-047235

(51) Int. Cl.
*C12M 1/36* (2006.01)
*C12M 1/38* (2006.01)
*C12M 3/00* (2006.01)
*C12M 1/34* (2006.01)
*C12M 1/00* (2006.01)

(52) U.S. Cl. ............... 435/303.1; 435/286.2; 435/287.3

(58) Field of Classification Search ............. 435/286.2, 435/287.3, 303.1, 809
See application file for complete search history.

(56) References Cited

U.S. PATENT DOCUMENTS 4,871,676 A * 10/1989 Yamada ................... 435/286.2

(Continued)

FOREIGN PATENT DOCUMENTS

FR 2 788 042 A1 7/2000

(Continued)

*Primary Examiner*—Walter D Griffin
*Assistant Examiner*—Lydia Edwards
(74) *Attorney, Agent, or Firm*—Kratz, Quintos & Hanson, LLP

(57) ABSTRACT

The invention provides a culture apparatus or a reserving stock room which receives a lot of culture vessels without vibration. The culture apparatus or the reserving stock room is provided with storage shelves (12a, 12b, . . . ) for culture vessels arranged in a circular arc shape or an annular shape, and a carrying means (15) for taking in and out the culture vessels to an inner side of the circular arc shaped arrangement or the annular shaped arrangement from the storage shelves (12a, 12b, . . . ). Further, the culture apparatus or the reserving stock room is provided with storage shelves (12a, 12b, . . . ) for culture vessels arranged on a table (13) in a circular arc shape or an annular shape, an air distribution port (39) provided in the table (13) such that an air in an inner side of the circular arc shaped arrangement or the annular shaped arrangement flows from a lower side to an upper side, and a circulation passage (36) for returning the air sucked from an upper side within a stock room to the distribution port (39) via a lower side within the stock room.

2 Claims, 3 Drawing Sheets

U.S. PATENT DOCUMENTS

| | | | | |
|---|---|---|---|---|
| 5,470,744 A | * | 11/1995 | Astle | 435/286.7 |
| 6,129,428 A | * | 10/2000 | Helwig et al. | 312/114 |
| 2004/0147012 A1 | * | 7/2004 | Yokoi et al. | 435/287.3 |

FOREIGN PATENT DOCUMENTS

| | | |
|---|---|---|
| JP | 52-66692 | 6/1977 |
| JP | 3-236769 | 10/1991 |
| JP | 7-87956 | 4/1995 |
| JP | 11-89559 | 4/1999 |
| JP | 2000-93156 | 4/2000 |
| JP | 2000093156 A * | 4/2000 |
| JP | 2000-135048 | 5/2000 |
| JP | 2001-299325 | 10/2001 |
| JP | 2001-352934 | 12/2001 |
| WO | WO 99/15905 | 4/1999 |
| WO | WO 01/53839 A1 | 7/2001 |

* cited by examiner

RADIAL LINE

CULTURE DEVICE AND STORAGE CONTAINER

BACKGROUND OF THE INVENTION

The present invention relates to a reserving stock room for reserving bacteria or the like, or a culture apparatus for culturing the bacteria or the like, for example, relates to an apparatus or a reserving stock room called as an automatic culture system, a blood reserving stock room, a frozen blood plasma reserving stock room, a drug medicine reserving stock room and the like.

There has been a culture apparatus for culturing the bacteria or the like structured such that a lot of micro plates forming a culture vessel for the bacteria or the like are received in a stock room for simultaneously culturing a lot of bacteria or the like by a single apparatus, and the micro plates are moved within the stock room by a carrying means. In recent days, this type of culture apparatus is required from market.

One example of this type of culture apparatus is disclosed in Japanese Unexamined Patent Publication No. 11-89559. Further, it is disclosed also in U.S. Pat. No. 6,129,428.

A description will be given of one example of the culture apparatus mentioned above with reference to FIG. 3.

In this example, a robot arm 7 transfers the culture vessel (the micro plate) to the carrying means within the culture apparatus from an external portion.

Storage shelves 2a, 2b and 2c for the culture vessels 5 are placed within the stock room of the culture apparatus 1. Further, the storage shelves 2a, 2b and 2c are arranged on a rotating table so as to form a circular arc. A plurality of culture vessels 5 are inserted to the respective shelves 2a, 2b and 2c in a vertical direction so as to be received therein.

A carrying mechanism (a carrying means) 4 inserts or takes out the culture vessel 5 to or from an optional height position of the storage shelves.

A carrying port 6 is provided in a back surface of the culture apparatus 1, and communicates an interior side of the stock room of the culture apparatus with an exterior side of the stock room. The carrying port 6 is provided with a shutter mechanism for opening and closing the carrying port 6, and is opened at a time of transferring the culture vessel 5 between the robot arm 7 corresponding to the external carrying mechanism and the carrying mechanism 4.

In order that the carrying mechanism 4 takes out the culture vessel received at the optional position of the storage shelves, first, the rotating table 3 is rotated, and the storage shelf in which the culture vessel is received is moved in front of the carrying mechanism 4.

Next, the carrying mechanism 4 is vertically moved to the height at which the culture vessel to be taken out is received.

Next, the carrying arm is extended and the carrying arm is inserted to a space below the culture vessel. Thereafter, the carrying mechanism 4 is slightly moved upward so as to lift up the culture vessel. Accordingly, the culture vessel floats up from the storage shelf.

Then, the carrying arm is retracted so as to completely take out and break away the culture vessel mounted on the carrying arm from the storage shelf.

Next, the carrying mechanism 4 is vertically moved to the height of the carrying port 6, and is horizontally rotated while keeping the height such as to face to the carrying port 6. Next, the shutter in the carrying port 6 is opened.

Further, the carrying arm is extended, and the culture vessel is taken out from the carrying port 6 to the external portion.

The robot arm 7 grips the culture vessel taken out to the external portion, and brings out to the external portion.

Thereafter, the carrying apparatus 4 retracts the carrying arm, turns in the horizontal direction so as to face to the storage shelf, and closes the shutter of the carrying port 6.

When bringing out one culture vessel to the external portion from the inner side of the stock room or receiving one culture vessel within the stock room from the external portion as mentioned above, all of the storage shelves 2a, 2b and 2c are rotated together with the table 3.

Since the other all culture vessels are simultaneously rotated together with the table 3 every time when the culture vessel is taken in and out, all the culture vessels received in the shelves 2a, 2b and 2c are vibrated, so that a stationary state of the culture vessel is almost lost. In the case of culturing periphytic cells, the cells breed normally by adhering the culture to a wall surface of the culture vessel.

However, the vibration of the culture vessel mentioned above generates a stress against bringing up the cells such as the bacteria or the like.

Further, since the culture is very frequently taken in and out, it is desired to make the carrying motion at a time of taking in and out the culture vessel higher.

However, taking the vibration of the culture vessel into consideration, it is impossible to make the rotation speed of the table 3 higher blindly.

The conventional culture apparatus with the carrying mechanism utilizes a rotary type storage shelf for the culture vessel. Accordingly, it is necessary to turn the whole of the shelf so as to move in front of the carrying means every time when one culture vessel is taken in and out. Therefore, the culture vessel frequently vibrates and there is a case that the cells can not be easily adhered to the vessel.

The present invention is provided with a carrying mechanism which automatically carries the culture vessel to the storage shelf, and the conventional culture apparatus with the carrying mechanism utilizes the rotary type storage shelf for the culture vessel. Accordingly, it is necessary to turn the whole of the shelf so as to move in front of the carrying means in order to take in and out one culture vessel. Therefore, the culture vessel frequently vibrates, and there is a case that the cells can not be normally adhered to the vessel.

SUMMARY OF THE INVENTION

The present invention is provided with storage shelves 12a, 12b, . . . which are arranged in a circular arc shape or an annular shape, and receiving a plurality of culture vessels in a vertical direction, and a carrying means 15 for taking in and out the culture vessels to an inner side of the circular arc shaped arrangement or the annular shaped arrangement from the storage shelves.

Further, the present invention is characterized in that the present invention is provided with storage shelves 12a, 12b, . . . for culture vessels which are arranged in a circular arc shape or an annular shape, a table (a pedestal) 13 supporting the storage shelves, an air distribution port 39 provided in the table 13 for circulating an air in an inner side of the circular arc shaped arrangement or the annular shaped arrangement from a lower side to an upper side, and a circulation passage 36 for returning the air sucked from an upper side within a stock room to a lower side within the stock room.

Further, the present invention is characterized in that a carrying port of the culture vessel is arranged at a position on a radial line of the circular arc shaped arrangement or the annular shaped arrangement so as to be in contact with a concentric circle of the circular arc shaped arrangement or the annular shaped arrangement.

Further, the present invention is characterized in that a door for sealing the stock room is provided, and a carrying door smaller than the door is provided in the same side as the door.

DETAILED DESCRIPTION OF THE PREFERRED EMBODIMENT

A description will be given of a first embodiment in accordance with the present invention with reference to FIGS. 1 and 2.

Figure 1:
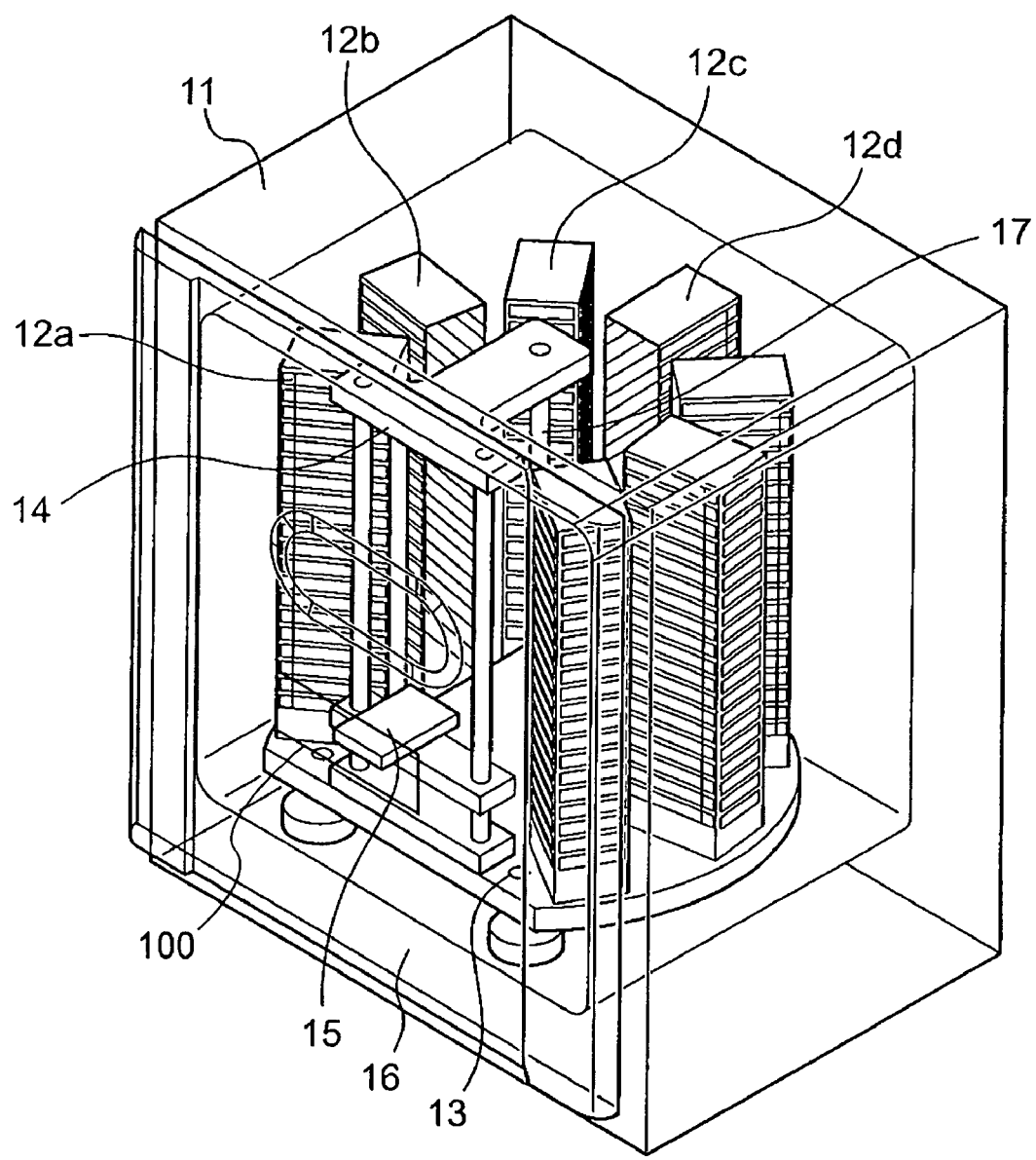
FIG. 1 is a perspective view of a culture apparatus in accordance with a first embodiment of the present invention while partly seeing through, FIG. 2 is a cross sectional view of the first embodiment as seen from an upper surface thereof.

FIG. 1 is a view of a culture apparatus while partly seeing through.

Storage shelves 12a, 12b, 12c, . . . are arranged in an inner portion of a culture apparatus 11 so as to be formed in a circular arc shape (or an annular shape). The storage shelves 12a, 12b, 12c, . . . are placed on a table (a pedestal) 13, each of the storage shelves is provided with a plurality of slots in a vertical direction, and each of the slots has a structure which can insert or take out a culture vessel.

The table 13 does not rotate during the culturing and the movement of the culture material (the culture vessel 18).

Accordingly, the shelves 12a, 12b, 12c, . . . do not move, and the culture vessel does not vibrate.

A support portion 14 vertically supports an elevation shaft 17. A carrying mechanism (a carrying means) 15 turns around the elevation shaft 17, and vertically moves. The culture vessel 18 in which the culture material is adhered to a wall surface is inserted to or taken out from a predetermined slot position in a predetermined storage shelf on the basis of the movement of the carrying mechanism 15.

A door 16 is provided with a carrying port 100 for transferring the culture vessel with respect to a carrying mechanism in an external portion.

Figure 2:
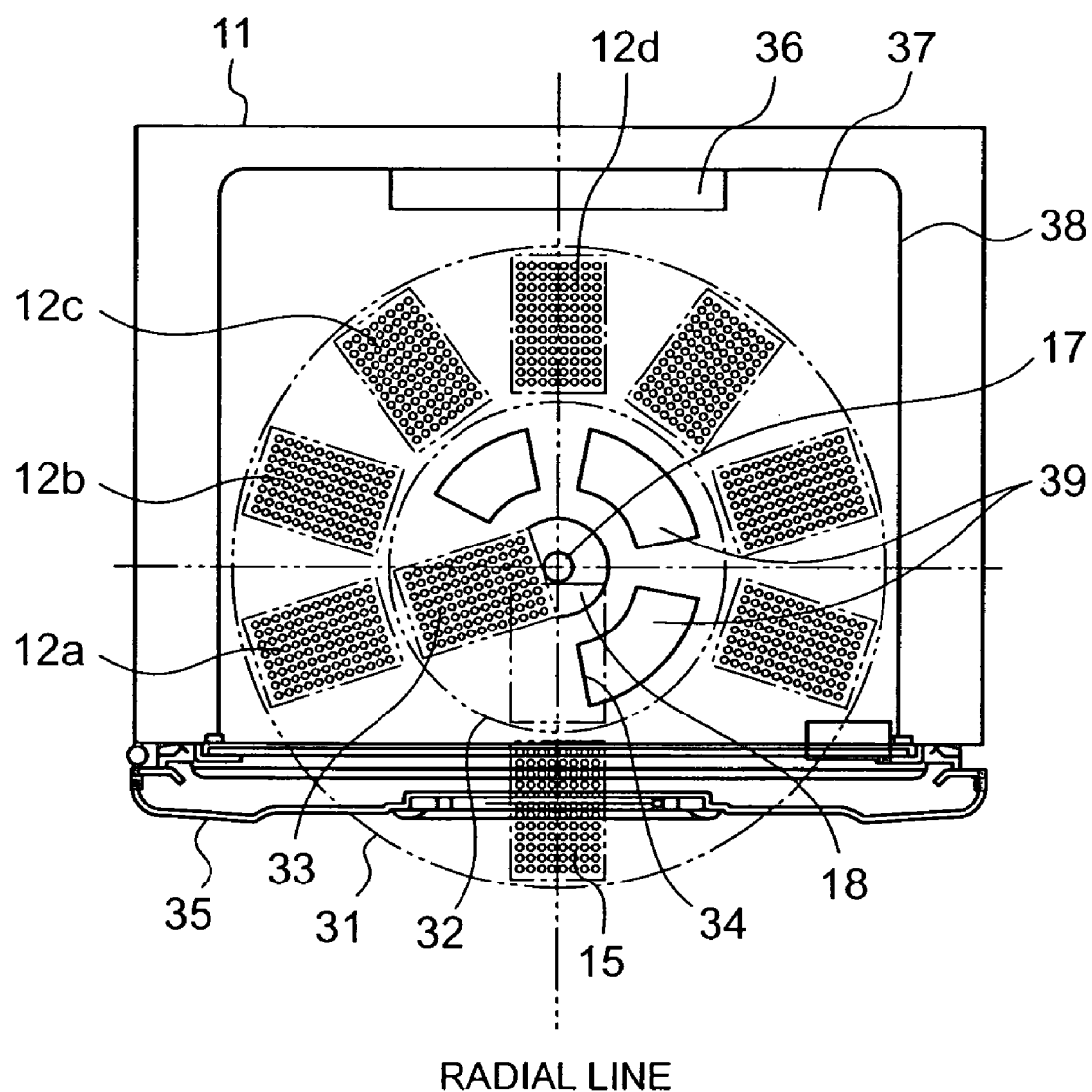
Figure 3:
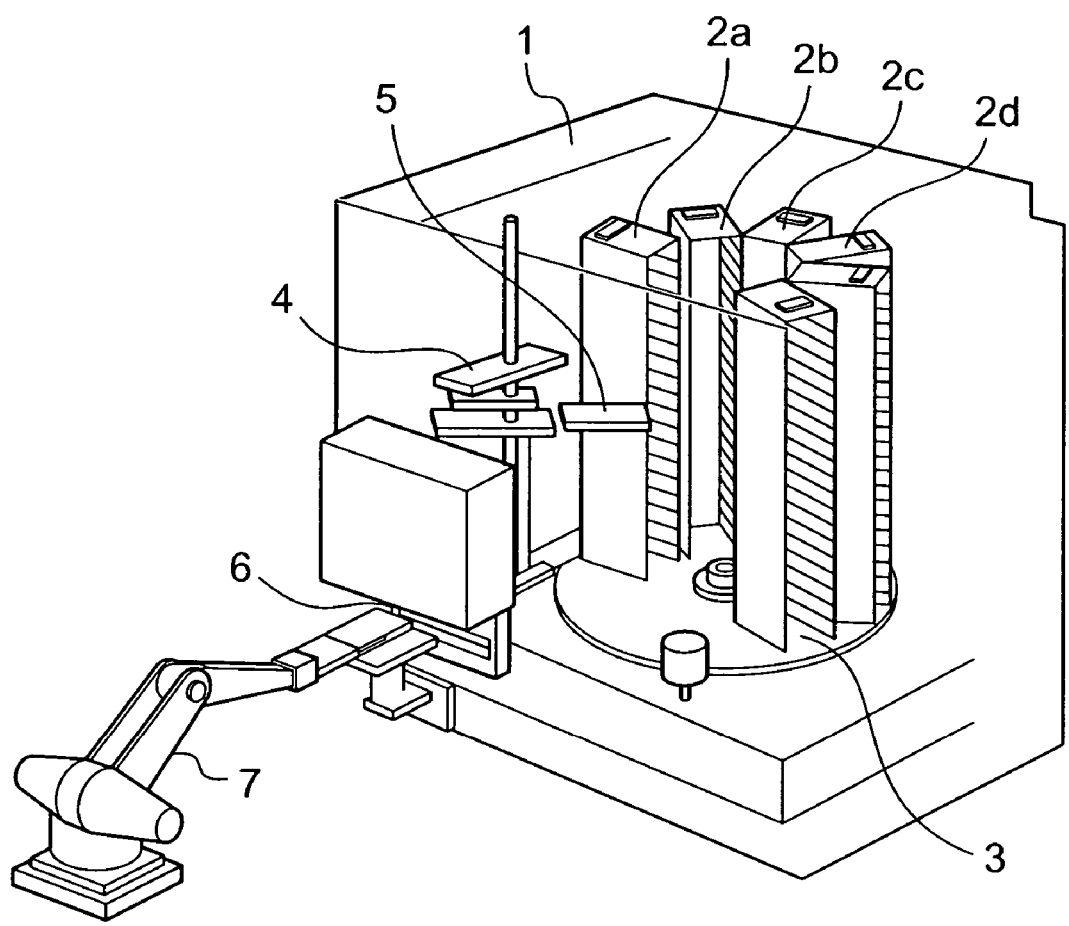
FIG. 3 is a perspective view showing a conventional culture apparatus.

FIG. 2 is a view as seen from an upper surface.

The storage shelves 12a, 12b, 12c, . . . holding the culture vessel 18 are arranged on the table such as to structure circular arcs 31 and 32 as a whole.

The carrying mechanism 15 is guided (not shown) so as to freely move in a vertical direction, and is provided with a thread groove fitted to a screw thread formed in an outer periphery of the elevation shaft 17. Accordingly, a rotation force generated in the thread groove of the carrying mechanism 15 by turning the elevation shaft 17 is converted into a force in a vertical direction (a moving force) so as to move the carrying mechanism 15 in the vertical direction. Since the elevation shaft 17 is rotated by a step motor, and a rotation speed of the elevation shaft 17 (substantially corresponding to a vertical height position of the carrying mechanism) is in proportion to a step number output to the step motor, the vertical height of the carrying mechanism 15 can be controlled by changing an output phase (CW: clockwise rotation, CCW: counterclockwise rotation) of a step to the step motor so as to rotate the step motor in the CW side or the CCW side.

When moving the carrying mechanism 15 to the slot in which a desired culture vessel at a desired height of a desired storage shelf is received, the step number and the output phase which are required for moving the carrying mechanism 15 from the current step number to the slot at the desired height are calculated by a micro computer or the like, and thereafter, the calculated step number is output to the step motor so as to move the carrying mechanism 15 in the vertical direction.

A guide for moving the elevation shaft 17 (including the step motor for rotating the shaft), and the carrying mechanism 15 in the vertical direction is provided on a table (not shown) turning around the same center shaft as the center shaft of the elevation shaft 17. The opposing storage shelf (or the desired slot) to the carrying mechanism 15 can be changed on the basis of the rotation of the table.

Since the table is structured in the same manner as that of the elevation shaft 17 such that the table can be rotated by the step motor for the storage shelf and the gear, the carrying mechanism 15 can be rotated to the opposing position to the desired storage shelf by changing the step number and the output phase output to the step motor for the storage shelf.

In other words, the following three means can be considered as a means for moving the carrying mechanism 15 to the opposing position to the desired slot (the desired culture vessel).

(1) Rotating the carrying mechanism 15 to the desired storage shelf after aligning the height of the carrying mechanism 15.

(2) Aligning the height of the carrying mechanism 15 after rotating the carrying mechanism 15 to the desired storage shelf.

(3) Rotating the carrying mechanism 15 at the same time of aligning the height.

However, the gist of the present invention is not changed by using any procedure.

In this case, aligning an initial value of the step motor and the step motor for the storage shelf is preferably carried out at least at a time of manufacturing the culture apparatus in accordance with the present invention, however, may be structured such as to be periodically carried out after installing (after using) the culture apparatus.

After the carrying mechanism 15 is moved to the opposing position to the culture vessel received in the desired slot at the desired height in the desired storage shelf, in the manner mentioned above, the carrying mechanism 15 extends the arm provided in the carrying mechanism 15 so as to insert to the lower portion of the culture vessel, and next outputs a desired number of pulses to the step motor of the elevation shaft 17 so as to slightly ascend the arm of the carrying mechanism 15 and lift up the culture vessel from the slot. Next, a state 33 shown in FIG. 2 is established by retracting the arm.

In this case, the arm in the carrying mechanism 15 can employ a general purpose structure for expanding and contracting by using a drive force of the motor (or the step motor or the like).

Next, the pulse number and the output phase which are output to the step motor and the step motor for the storage shelf are controlled such that the carrying mechanism 15 is moved to a state 34 shown in FIG. 2.

The arm is extended here, and the culture vessel can be transferred with respect to the external carrying device.

In accordance with this embodiment, since the carrying mechanism does not pass above the other culture vessels during the carrying operation, a damage due to an accidental drop or the like is slim. Further, since a motion is reduced, it is possible to make the carrying speed high.

Further, since the carrying mechanism operates in an inner side of the circular arc 31 and in an outer side of the circular arc 32, no extra operation space is required. Accordingly, a lot of culture materials can be received in the small-sized culture apparatus.

Further, since the carrying port is arranged on the radial line of the circular arcs 31 and 32 so as to be in contact with the concentric circle of the circular arcs 31 and 32, it is possible to bring out the culture vessel from the carrying port only by extending the arm of the carrying mechanism 15, and no specific means is required for moving the culture vessel to the carrying port.

Since a plurality of storage shelves are arranged so as to form the circular arc shape having the open front surface, the states of the culture vessel and the carrying mechanism can be easily observed, and a maintenance can be easily carried out.

The air within the stock room 38 including the inner sides of the circular arcs of the storage shelves 12a, 12b, 12c, . . . arranged so as to for the circular arcs 31 and 32 ascends within the culture space including the culture vessel from the lower side to the upper side through the through hole (a distribution port) 39, is recovered in the circulation passage 36, and carries out a downward circulation. Accordingly, it is possible to evenly maintain the temperature and the gas concentration within the stock room. At this time, a blower apparatus may be provided in the lower portion of the through hole or the circulation passage 36 in order to promote the air circulation.

As described above, since the present invention does not rotationally move the storage shelves holding the culture vessels for carrying the culture materials, it is possible to minimize the stress applied to the cells due to the vibration. The culture materials are arranged in the circular arc shape, and the carrying mechanism is arranged in the inner side of the circular arc arrangement of the culture materials. Accordingly, it is possible to achieve the reduction of the carrying time and reduction of the vibration. Further, since no rotating table is provided, it is easy to make the speed of the carrying mechanism high.

Further, since the carrying mechanism is arranged in the inner side of the circular arc, it is possible to reduce the extra space required for placing and operating the carrying mechanism, so that a lot of culture materials can be received even in the small-sized culture apparatus.

The temperature distribution within the stock room tends to be deteriorated in the case that the storage materials are received densely, however, in the present invention, since the air flow passage is structured in the inner side annularly surrounded by the storage shelves, the temperature distribution is not deteriorated.

As described above, in accordance with the present invention, since the shelves for holding the culture materials are not moved for carrying the culture materials, it is possible to minimize the stress applied to the cells due to the vibration.

What is claimed is:

1. A culture apparatus or a reserving stock room comprising:
   storage shelves (12a, 12b, . . . ) for culture vessels arranged in a circular arc shape having an open front surface, in the apparatus or stock room;
   a table (13) for supporting said storage shelves (12a, 12b, . . . ), wherein said table (13) does not rotate; and
   carrying means (15) for carrying said culture vessels arranged inside of the circular arc shape; characterized by
   a door (16) for sealing the apparatus or stock room, the door (16) being arranged in the side on which the circular arc shape opens; and
   a carrying port for receiving said culture vessels from outside said apparatus or stock room and passing said culture vessels to outside said apparatus or stock room; wherein
   the carrying port of said culture vessel is arranged in the door (16) such that the carrying port is disposed inside of an extended radial line of said circular arc shape;
   the carrying means (15) can rotate to face a predetermined storage shelf; and
   the carrying means (15) accesses the culture vessel 18 from inside of the circular arc shape.

2. A culture apparatus or a reserving stock room according to claim 1, further comprising:
   an air distribution port (39) provided in said table (13) such that an air in an inner side of said circular arc shaped arrangement or said annular shaped arrangement flows from a lower side to an upper side; and
   a circulation passage (36) for returning the air sucked from an upper side within a stock room to said distribution port (39) via a lower side within the stock room.

* * * * *